United States Patent [19]

Mönch et al.

[11] Patent Number: 5,083,805
[45] Date of Patent: Jan. 28, 1992

[54] EQUIPMENT TROLLEY

[75] Inventors: Harry Mönch, Knittlingen; Willi Weisert, Oberderdingen, both of Fed. Rep. of Germany

[73] Assignee: Riwoplan Medizintechnische Einrichtungsgesellschaft mbH, Knittlingen, Fed. Rep. of Germany

[21] Appl. No.: 514,907

[22] Filed: Apr. 26, 1990

[30] Foreign Application Priority Data

Jun. 3, 1989 [DE] Fed. Rep. of Germany ....... 3918162

[51] Int. Cl.⁵ .............................................. B62B 3/02
[52] U.S. Cl. ................................. 280/47.35; 211/191; 280/79.3
[58] Field of Search ................. 280/47.35, 47.34, 79.3, 280/79.11; 312/250, 306, 245, 195; 211/133, 151, 13, 70.6, 153, 189, 191, 187; 108/106, 107

[56] References Cited

U.S. PATENT DOCUMENTS

| | | | |
|---|---|---|---|
| 2,830,825 | 4/1958 | Webber et al. | 280/79.3 |
| 3,323,656 | 6/1967 | Weiss et al. | 211/153 |
| 4,512,591 | 4/1985 | Plante | 211/189 X |
| 4,763,799 | 8/1988 | Cohn et al. | 211/187 |
| 4,822,116 | 4/1989 | Relyea et al. | 312/250 |
| 4,875,696 | 10/1989 | Welch et al. | 280/47.34 |

FOREIGN PATENT DOCUMENTS 2042880 10/1980 United Kingdom ................ 211/189

Primary Examiner—Andres Kashnikow
Assistant Examiner—Michael Mar
Attorney, Agent, or Firm—Panitch Schwarze Jacobs & Nadel

[57] ABSTRACT

An equipment trolley, particularly for transporting and/or holding medical instruments, equipment and the like, can, by using standardized components such as carrier trays, drawer blocks and the like, be customized to suit its intended purpose, and to prevent the transmission of germs, all the components are sheathed by formed plastics members of complementary configuration to said components, thus protecting the metal parts against contact with harsh media likely to cause corrosion.

4 Claims, 3 Drawing Sheets

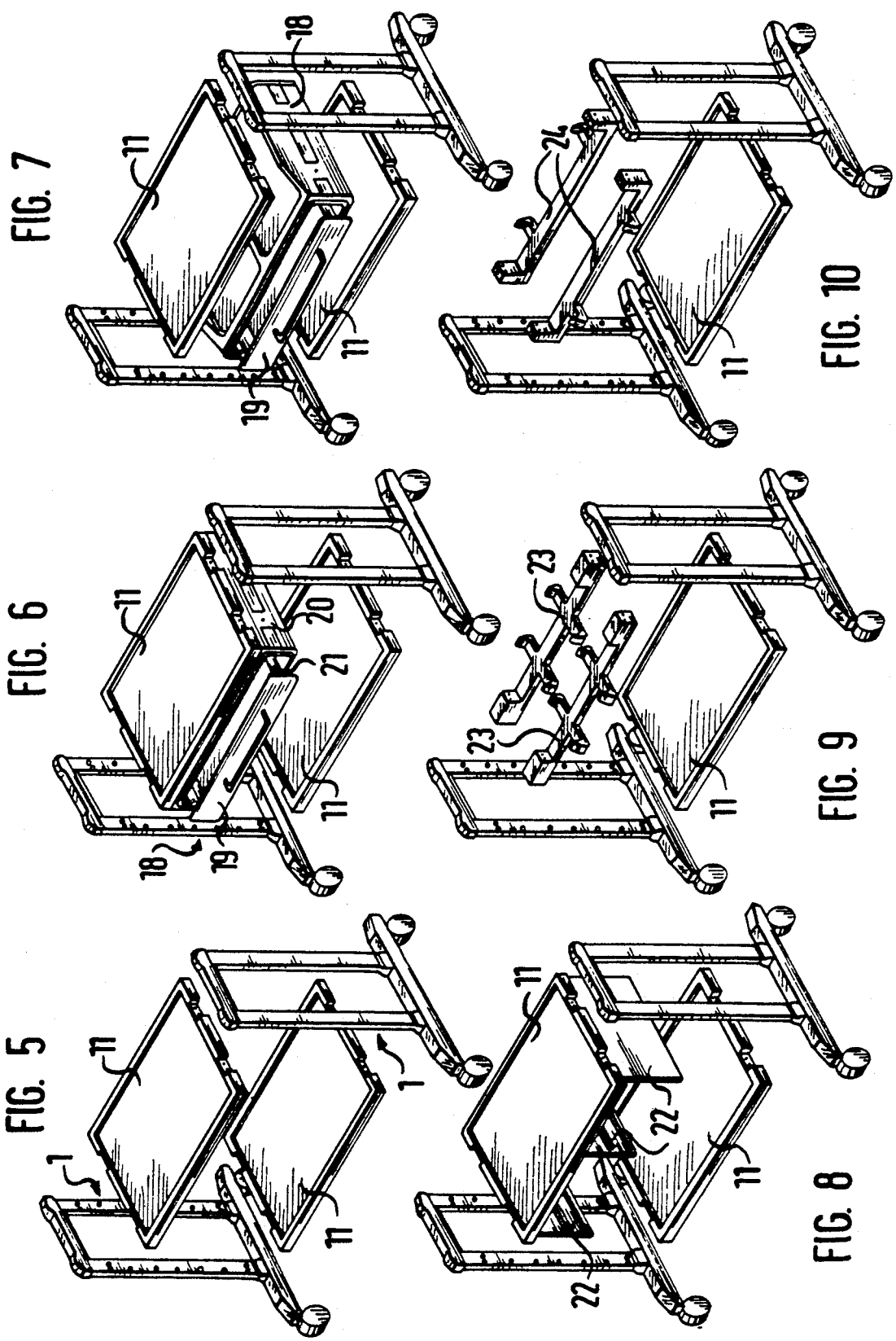

EQUIPMENT TROLLEY

BACKGROUND OF THE INVENTION (a) Field of the Invention

The invention relates to an equipment trolley, particularly for transporting and/or holding medical instruments, equipment and the like, comprising a supporting framework resting on casters which, by using standardized components such as carrier trays, drawer blocks for one or more drawers, and the like, can be customized to suit its intended purpose.

(b) Description of the Prior Art

There are known equipment trolleys of this kind of a wide variety of designs in which the external configuration of the trolley and the layout, construction and finish of the storage surfaces, drawers and so on are adapted to the particular intended purpose. At the same time, to prevent the unintentional transmission of germs, the surfaces of equipment trolleys of this kind which are employed in clinical practice are provided with an electroplated or painted covering or even with a plastics coating. The mechnical strength which has to be ensured in everyday use is generally obtained by welding together the individual parts, and in particular the load-bearing parts such as uprights, struts and the like, so that the main body forms an indissoluble structural unit. It is only accessories or separable items such as slides or doors which are screwed on.

Hence, the disadvantage from which prior art trolleys suffer lies in the fact that they are usually developed and manufactured in direct conformity with their particular intended purpose, which means that it is only to a very limited degree that individual components can be used for other versions, thus producing a large number of mutually dissimilar components, which, in the final analysis, makes development and manufacture a very expensive business.

Another disadvantage of prior art trolleys lies in the sometimes unsatisfactory nature of their surfaces, which means that corrosive damage caused by harsh cleansers and/or disinfectants, humidity and spilled liquids causes incessant worsening of hygienic standards, resulting in the unintentional transmission of germs and the risks to the patient which this engenders.

Thus, the main object of the present invention is to provide an equipment trolley which is not only easy to customize to suit the particular purpose for which it is intended but which also has surfaces whose nature and configuration is such that any risk of the transmission of germs is counteracted to the greatest possible degree.

SUMMARY OF THE INVENTION

To this end, the present invention consists in an equipment trolley, particularly for transporting and/or holding medical instruments, equipment and the like, comprising a supporting framework resting on casters which, by using standardized components such as carrier trays, drawer blocks for one or more drawers, and the like, can be customized to suit its intended purpose, characterised in that the load-bearing components in particular comprise metal parts securable to the supporting framework, all of which are sheathed by formed plastics members of complementary configuration which enclose the said metal parts.

By means of the invention the advantages thereby achievable lie, in particular, in the fact that any direct contact between a liquid medium such as disinfectant and a metal part at risk from corrosion is prevented. As well as this advantage, there is also the fact that because standardized components are used, the possibility exists of replacing individual parts without any difficulty if damage occurs or if the fitness for use of the trolley is impaired due to wear.

In a preferred embodiment of the invention, the supporting framework may comprise two main body sidemembers formed by two vertically upstanding supporting columns which are releasably connected together by a top cross-member which also acts as a handle and a bottom cross-member which is fitted with the casters in the region of both of its ends. At the same time, the supporting columns may be provided with holding means arranged in a specific pattern for the fixing of the said components. The formed plastics members which sheathe the supporting columns may be surrounded, in the region of the joint to the cross-member carrying the casters, by a gaiter which forms a sealed connection to the formed plastics member which covers the said cross-member. At the other end, the formed plastics member sheathing the supporting columns may be overlapped by the formed plastics member which covers the cross-member formed as a handle.

In a further embodiment, each holding tray may include a metal reinforcing plate which is stiffened in the longitudinal direction from the underside by cross-members, the reinforcing plate being encased with a seal between a functional surface and a formed plastics member which is adapted to the shape of the reinforcing plate and the cross-members.

Where drawers are fitted, the drawer blocks holding them may comprise an inner and an outer formed plastics member between which stiffening elements and/or stiffening plates may be fitted. Both the drawers and the drawer block may however also be made from plastics material.

BRIEF DESCRIPTION OF THE DRAWINGS

In order that the invention may be more readily understood some embodiments thereof will now be described, by way of example, with reference to the accompanying drawings, in which:

FIG. 5 shows a first possible combination involving two holding trays, FIG. 6 shows a second possible combination involving two holding trays with a drawer block arranged between them, FIG. 7 shows a third possible combination involving a first holding tray, a drawer block and a second holding tray, with the various items spaced away from one another, FIG. 8 shows a fourth possible combination involving two trays spaced apart from one another with carrier elements arranged between them to hold disinfecting dishes for example, FIG. 9 shows a fifth possible combination involving one holding tray and two carrier elements to hold two large disinfecting containers, and FIG. 10 shows a sixth possible combination involving one holding tray and two carrier elements to hold a single disinfecting container of large capacity.

DESCRIPTION OF THE PREFERRED EMBODIMENTS

Figure 1:
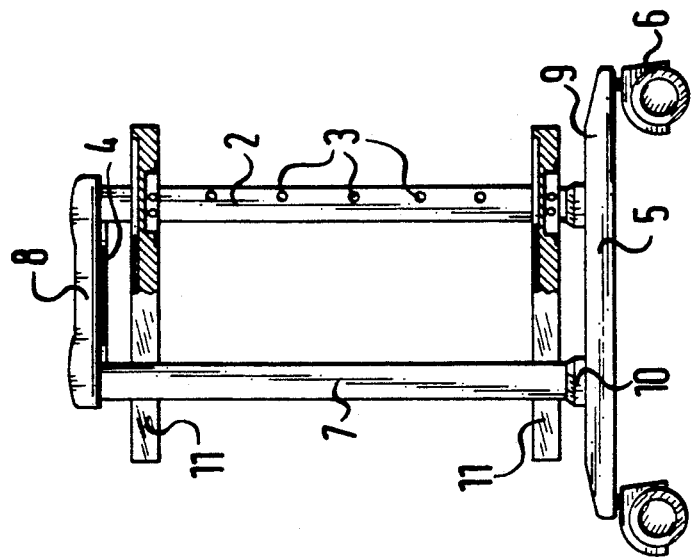
FIG. 1 is a front elevation of the simplest version of the main body of an equipment trolley constructed in accordance with the invention.
Figure 2:
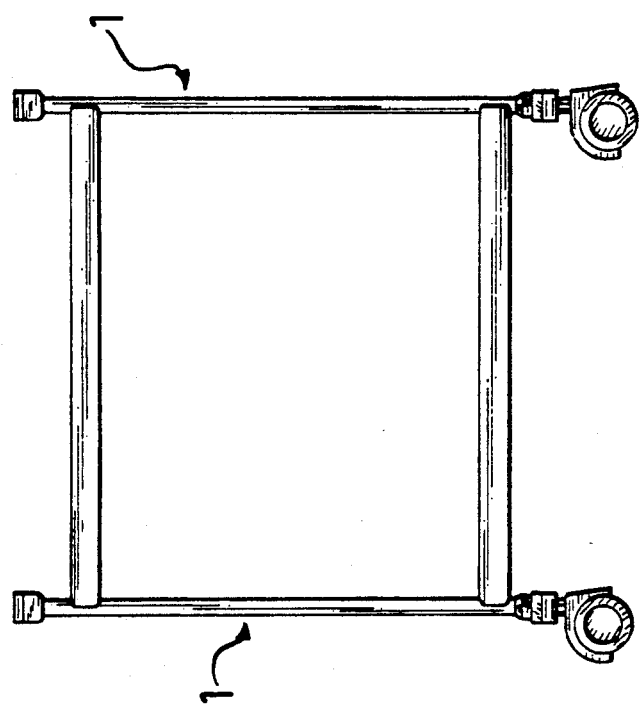
FIG. 2 is a side elevation of the main body shown in FIG. 1, partly in section.

Referring to the drawings, an equipment trolley according to the invention comprises, in essence, two main-body side-members 1 spaced apart from one another laterally. These in turn comprise two supporting columns 2 which are orientated vertically and parallel to one another, and which have holding means 3, in the form of threaded holes for example, arranged in a specific pattern. The two supporting columns 2 are connected together by a top cross-member 4 which also acts as a handle and by a bottom cross member 5, with the members 1,2,4 and 5 forming a supporting framework. The two bottom cross-members 5 are provided at each of their two diametrically opposed ends with casters 6 on which the supporting framework of the trolley rests to allow the trolley to be moved about. The connections between the supporting columns 2 and the cross-members 4 and 5 are of releasable design, although these items can only be disassembled by using tools.

For reasons of strength, parts 2,4 and 5 are made from metal and in view of hygienic requirements they are sheathed with formed plastics members 7, 8 and 9 of a complementary configuration. These members overlap one another sufficiently to effectively prevent any direct contact between the metal parts and liquid media. To stop liquids penetrating into the area of the joints between the bottom ends of the supporting columns 2 and the bottom cross-member 5, the formed plastics member 7 which surrounds the supporting column 2 has, in the region of this joint, a gaiter 10 which makes a sealed connection to the formed plastics member 9 surrounding the bottom cross-member 5.

Figure 3:
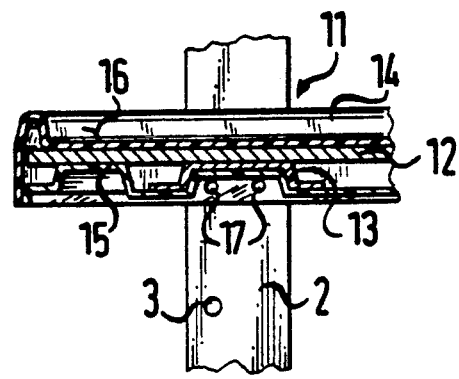
FIG. 3 is an enlarged detail showing the construction of a holding tray seen in FIG. 2.
Figure 4:
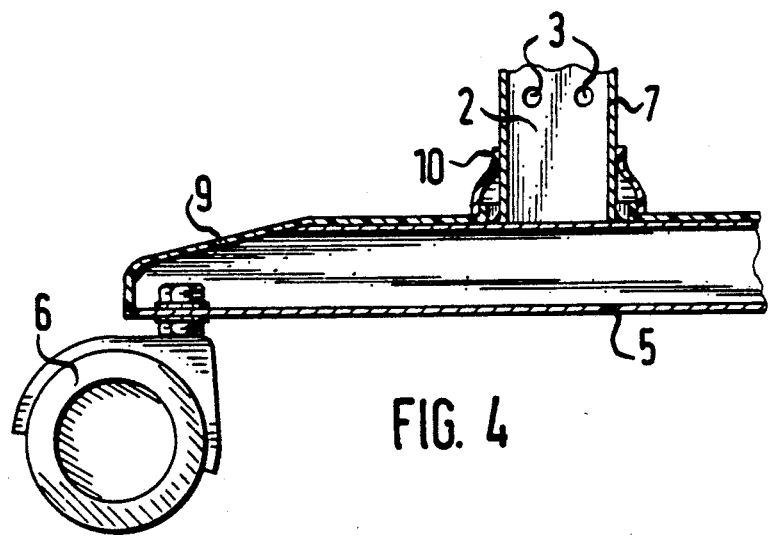
FIG. 4 is an enlarged detail showing a connection between a supporting column and a bottom cross-member.

The main-body side members 1 designed in this way form the lateral uprights for components selected to suit the intended purpose of the equipment trolley, the connections between said components and the side members 1 at the holding means 3 in the supporting columns 2 being made, in the simplest case, with screws. Among said components are a holding tray 11 which, as shown in FIG. 3, includes a reinforcing plate 12 which is stiffened in the longitudinal direction from the underside by cross-members 13 and which is encased in formed plastics members 14 and 15. Formed plastics member 14 fits around the side edges of reinforcing plate 12 and forms a functional surface 16, while formed plastics member 15 is matched to the underside of reinforcing plate 12 and to cross-members 13 and is welded at the edges to formed plastics member 14. Holding tray 11 is fixed to the supporting columns 2 via holes 17.

As shown in FIGS. 6 and 7, the components which can be used also include a drawer block 18 to hold drawers 19, which items may also be of sandwich construction similar to that described above. To this end, the drawer block 18 has an outer formed plastics member 20 and an inner formed plastics member 21, between which members may be situated stiffening elements and stiffening plates to improve mechanical strength. In line with the state of the art, the drawers 19 run on telescopic slides (not shown). The drawer block 18 is fixed to the supporting columns 2 in the same way as has already been described above. The drawers 19 too may be provided with stiffening elements. In FIG. 6, the drawer block 18 forms part of the upper tray 11, whereas in FIG. 7 it is separate from the tray.

In the versions intended for carrying disinfecting dishes which are shown in FIGS. 8,9 and 10, the holding trays 11 or even the supporting columns 2 may be fitted directly with the appropriate carrier elements 22,23 and 24. To carry weight-induced loads, these carrier elements too each have a metal main body (not shown) which is surrounded by a formed plastics member shaped to complement the main body. This being the case, the formed plastics members which fit around carrier elements 23 and 24 may be open at the bottom whereas carrier elements 22 are completely surrounded by their formed plastics members.

The formed plastics members 7 which sheathe the supporting columns 2 are so designed that all the holding means 3 are covered. Hence, to allow components to be fixed in position, the formed plastics members 7 must be provided with perforations, but only at those points behind which the appropriate holding means 3 are concealed.

It should be appreciated that the invention is not limited to the embodiments herein described but includes all modifications and variations falling within its scope. For example, in another embodiment of the equipment trolley according to the invention, it is conceivable for the formed plastics members to be immovable on the various metal main bodies in the manner of a shrink sleeve.

We claim:

1. An equipment trolley, particularly for transporting and/or holding medical instruments and equipment, the equipment trolley comprising a supporting framework resting on casters, the supporting framework comprising two main-body side-members, each formed by two vertically upstanding supporting columns which are releasably connected together by a top cross-member which also acts as a handle and a bottom cross-member having end regions which are fitted with said casters, the trolley having load-bearing components comprising metal parts which are securable to the supporting framework and all of which are sheathed by pre-formed plastic means of complementary configuration which enclose the metal parts for inhibiting the transmission of germs and preventing corrosive damage to the metal parts, wherein there is a joint between each supporting column and the respective bottom cross-member and wherein the pre-formed plastic means which sheathe the supporting columns have, in the region of the joint, a gaiter which forms a sealed connection to the preformed plastic means which covers the cross-member.

2. An equipment trolley particularly for transporting and/or holding medical instruments and equipment, the equipment trolley comprising a supporting framework resting on casters, wherein the trolley has load-bearing components comprising metal parts which are securable to the supporting framework and all of which are sheathed by formed plastic means of complementary configuration which enclose the metal parts for inhibiting the transmission of germs and preventing corrosive damage to the metal parts, and at least one instrument holding tray which includes an elongate reinforcing plate having an underside and being stiffened in the longitudinal direction from the underside by cross-members, the reinforcing plate being encased between an instrument holding surface covered by a pre-formed lower plastic means and another pre-formed upper plastic means which is adapted to the shape of the underside of the reinforcing plate and the cross-members.

3. An equipment trolley particularly for transporting and/or holding medical instruments and equipment, the equipment trolley comprising a supporting framework resting on casters, wherein the trolley has load-bearing components comprising metal parts which are securable to the supporting framework and all of which are sheathed by formed plastic means of complementary configuration which enclose the metal parts for inhibiting the transmission of germs and preventing corrosive damage to the metal parts, and at least one drawer block and at least one drawer held by the drawer block, the drawer block comprising a bottom, a first side and a second side, the bottom being generally perpendicular to each of the sides and the first side being generally parallel to the second side, wherein the drawer block and the drawer comprise an inner pre-formed plastic means and an outer pre-formed plastic means between which are fitted with at least one stiffening element and stiffening plate encased therebetween.

4. An equipment trolley according to claim 3 wherein at least one drawer and at least one drawer block are made from plastic material.

* * * * *